United States Patent
You et al.

(10) Patent No.: US 7,108,759 B2
(45) Date of Patent: Sep. 19, 2006

(54) METHOD FOR IMPROVED BOND STRENGTH IN AN ELASTOMERIC MATERIAL

(75) Inventors: Frederique You, Appleton, WI (US); Paul T. VanGompel, Hortonville, WI (US); Russell E. Thorson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/741,916

(22) Filed: Dec. 19, 2003

(65) Prior Publication Data
US 2005/0133144 A1 Jun. 23, 2005

(51) Int. Cl.
*B32B 37/00* (2006.01)

(52) U.S. Cl. ............... 156/73.1; 156/164; 156/229; 156/494; 156/580.1

(58) Field of Classification Search .......... 156/73.1, 156/161, 163, 164, 166, 196, 199, 200, 226, 156/227, 229, 269, 459, 461, 522, 580.1, 156/580.2, 442, 443, 444, 494, 495, 496; 425/174.2; 167/229, 269; 264/442, 443, 264/444
See application file for complete search history.

(56) References Cited

U.S. PATENT DOCUMENTS

| | | | |
|---|---|---|---|
| 4,333,978 A | 6/1982 | Kocher | |
| 4,713,132 A | 12/1987 | Abel et al. | |
| 4,720,415 A * | 1/1988 | Vander Wielen et al. ... | 428/152 |
| 4,758,293 A | 7/1988 | Samida | |
| 4,863,542 A | 9/1989 | Oshefsky et al. | |
| 5,087,320 A | 2/1992 | Neuwirth | |
| 5,096,532 A | 3/1992 | Neuwirth et al. | |
| 5,110,403 A | 5/1992 | Ehlert | |
| 5,376,198 A | 12/1994 | Fahrenkrug et al. | |
| 5,536,555 A * | 7/1996 | Zelazoski et al. ............ | 428/138 |
| 5,591,298 A | 1/1997 | Goodman et al. | |
| 5,660,679 A | 8/1997 | Rajala et al. | |
| 5,667,608 A | 9/1997 | Rajala et al. | |
| 5,707,470 A | 1/1998 | Rajala et al. | |
| 5,711,847 A | 1/1998 | Rajala et al. | |
| 5,733,411 A | 3/1998 | Bett | |
| 5,755,902 A | 5/1998 | Reynolds | |
| 5,817,199 A | 10/1998 | Brennecke et al. | |
| 5,868,153 A | 2/1999 | Cohen et al. | |
| 5,871,605 A | 2/1999 | Bett | |
| 6,123,792 A | 9/2000 | Samida et al. | |
| 6,372,067 B1 | 4/2002 | Kobayashi et al. | |
| 6,450,417 B1 | 9/2002 | Gipson et al. | |
| 6,454,890 B1 | 9/2002 | Couillard et al. | |
| 6,461,457 B1 | 10/2002 | Taylor et al. | |
| 6,517,650 B1 | 2/2003 | Couillard et al. | |
| 6,517,671 B1 | 2/2003 | Couillard et al. | |
| 6,533,879 B1 | 3/2003 | Quereshi et al. | |
| 6,537,401 B1 | 3/2003 | Couillard et al. | |
| 6,537,403 B1 | 3/2003 | Blenke et al. | |
| 6,540,854 B1 | 4/2003 | Couillard et al. | |
| 6,547,903 B1 | 4/2003 | McNichols et al. | |
| 6,555,731 B1 | 4/2003 | LaChapell et al. | |
| 6,562,166 B1 | 5/2003 | Molander et al. | |
| 6,613,171 B1 | 9/2003 | McNichols et al. | |
| 6,620,270 B1 | 9/2003 | Ehlert et al. | |
| 6,628,408 B1 | 9/2003 | Franklin et al. | |
| 2003/0188819 A1 | 10/2003 | Campbell et al. | |
| 2004/0020579 A1 * | 2/2004 | Durrance et al. ............ | 156/66 |

* cited by examiner

*Primary Examiner*—James Sells
(74) *Attorney, Agent, or Firm*—Brinks Hofer Gilson & Lione

(57) ABSTRACT

A method for increasing the bond strength of ultrasonic bonds in elastomeric materials comprising elongating the elastomeric materials prior to ultrasonically bonding the materials.

29 Claims, 8 Drawing Sheets

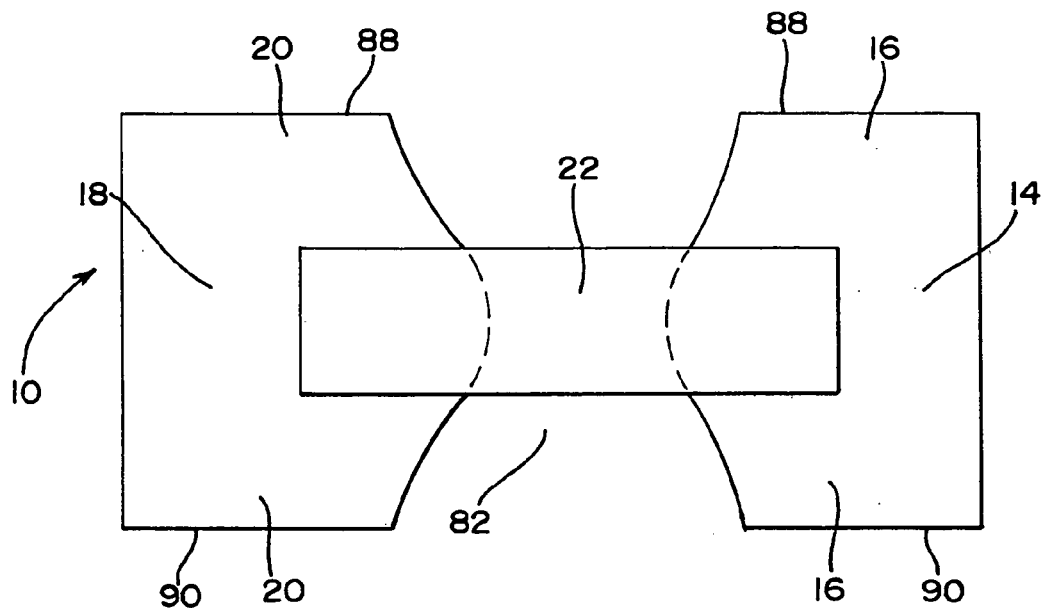
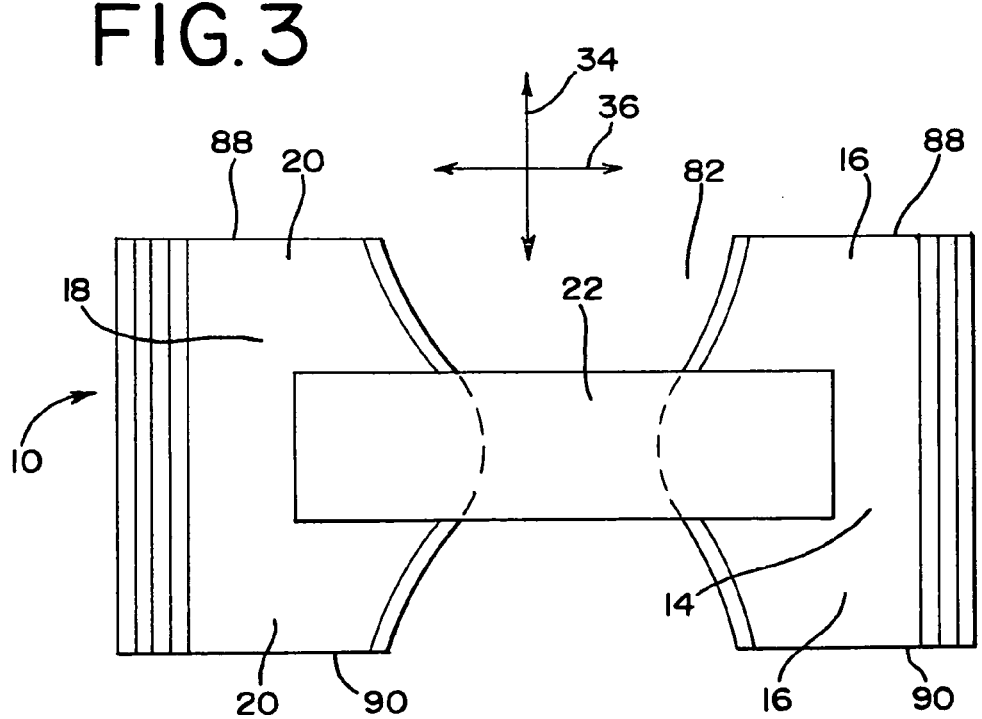

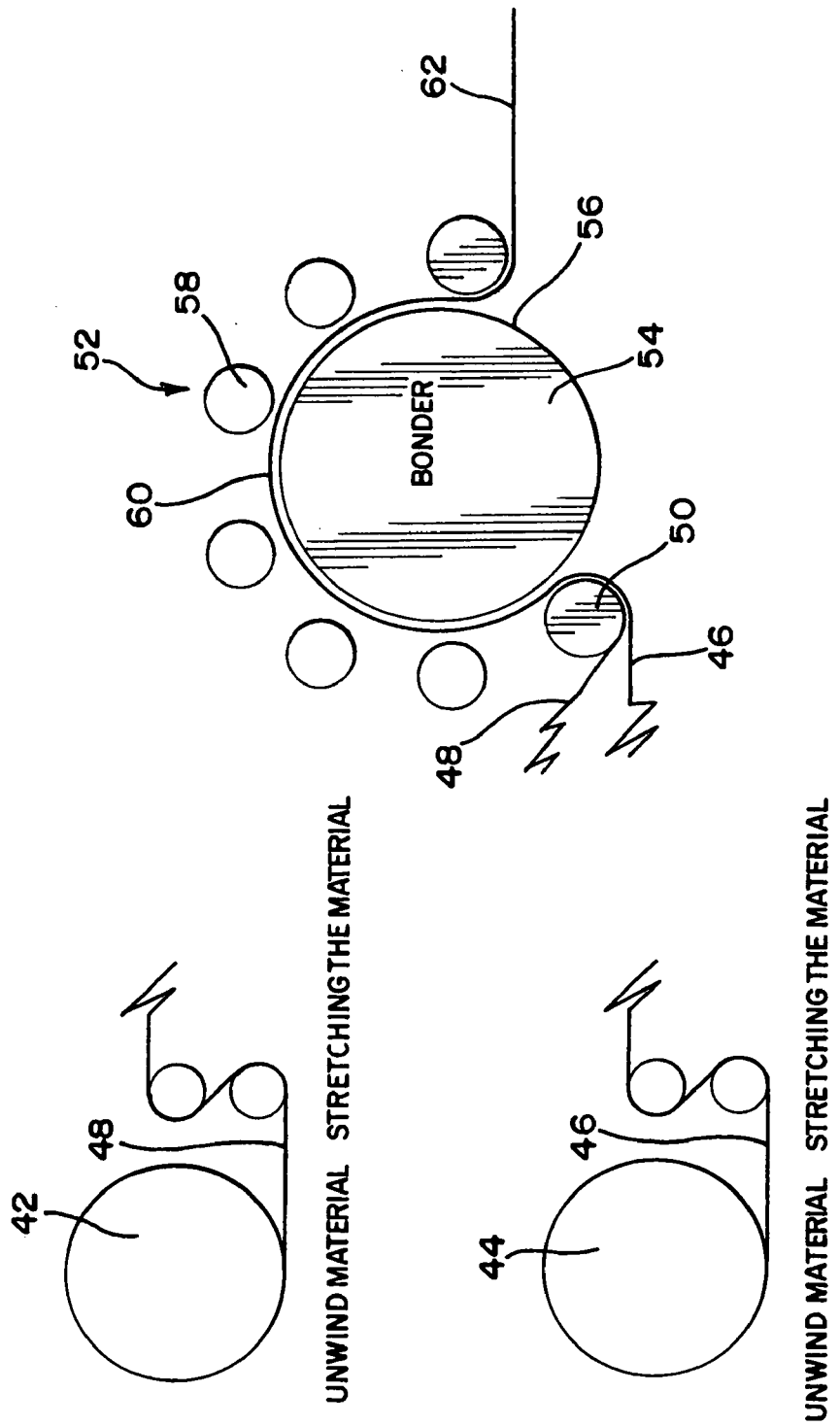

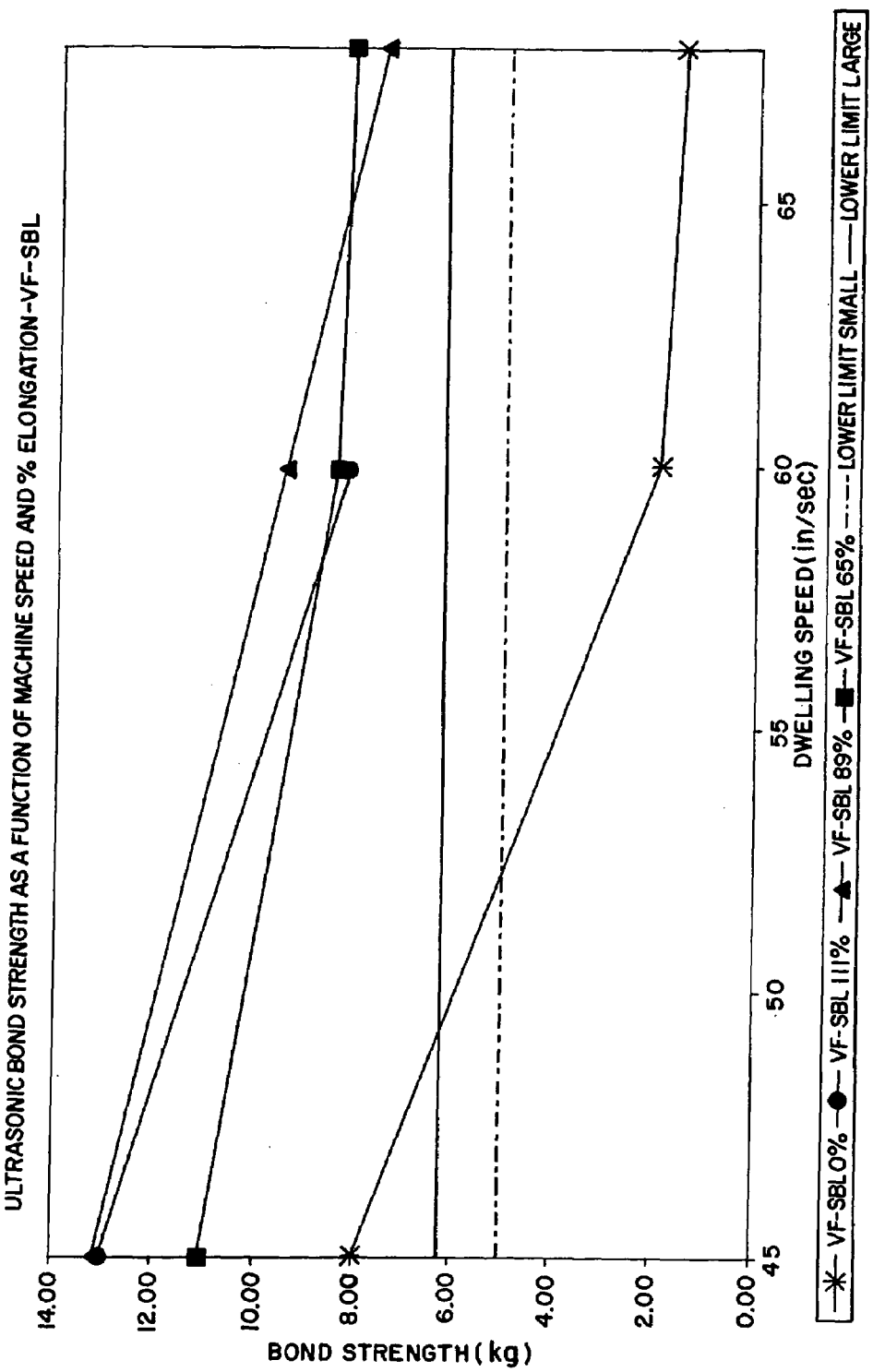

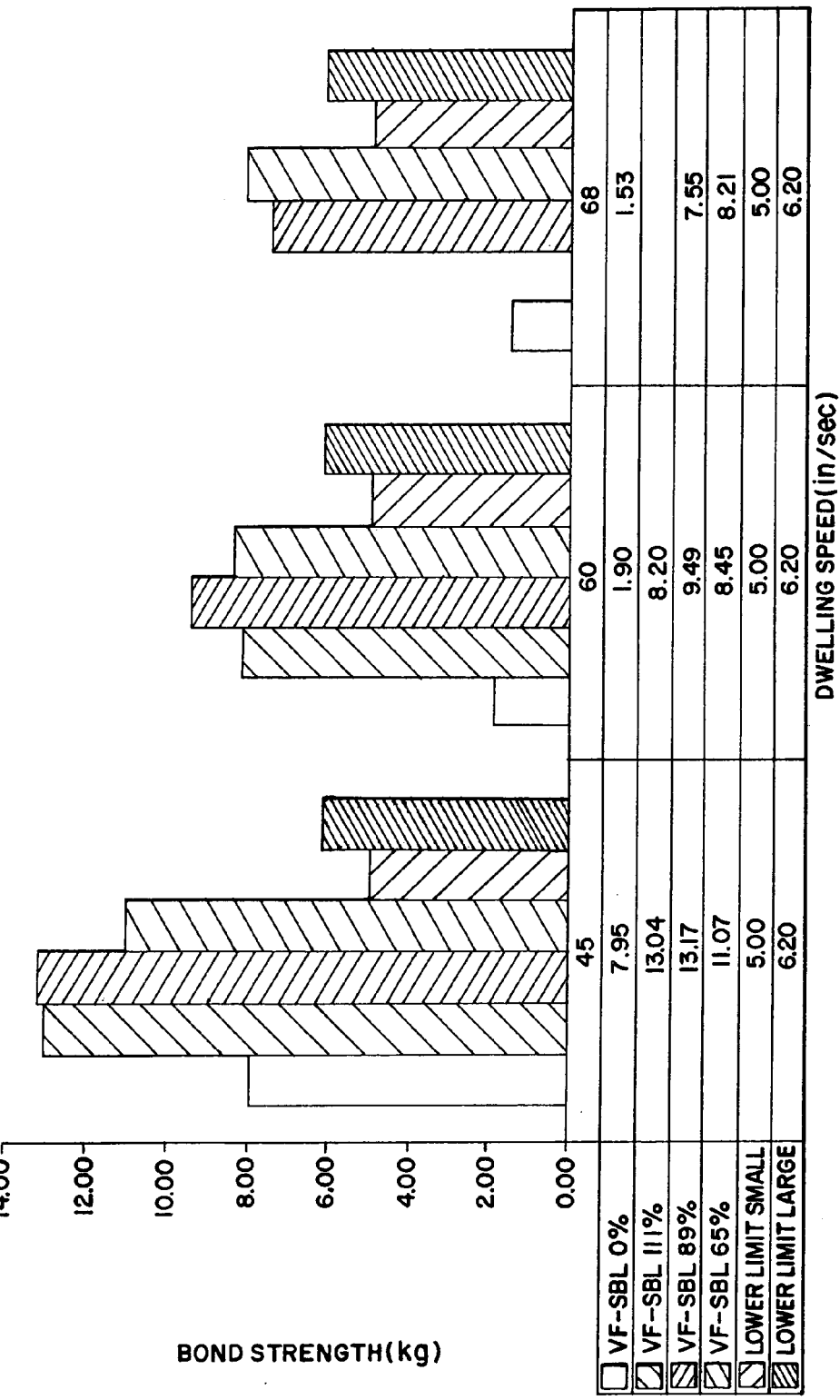
FIG. 7 ULTRASONIC BOND STRENGTH AS A FUNCTION OF MACHINE SPEED AND % ELONGATION-VF-SBL

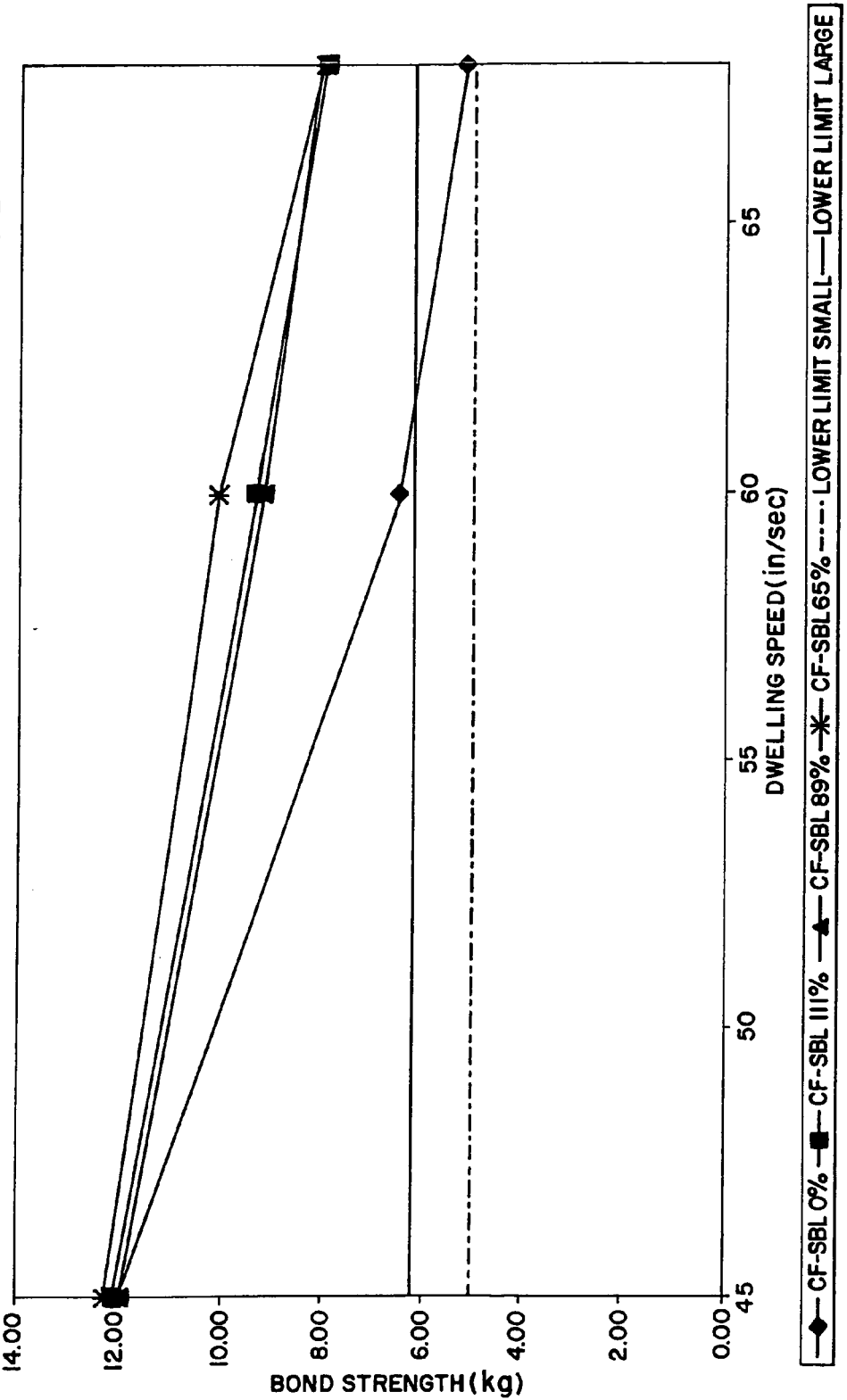

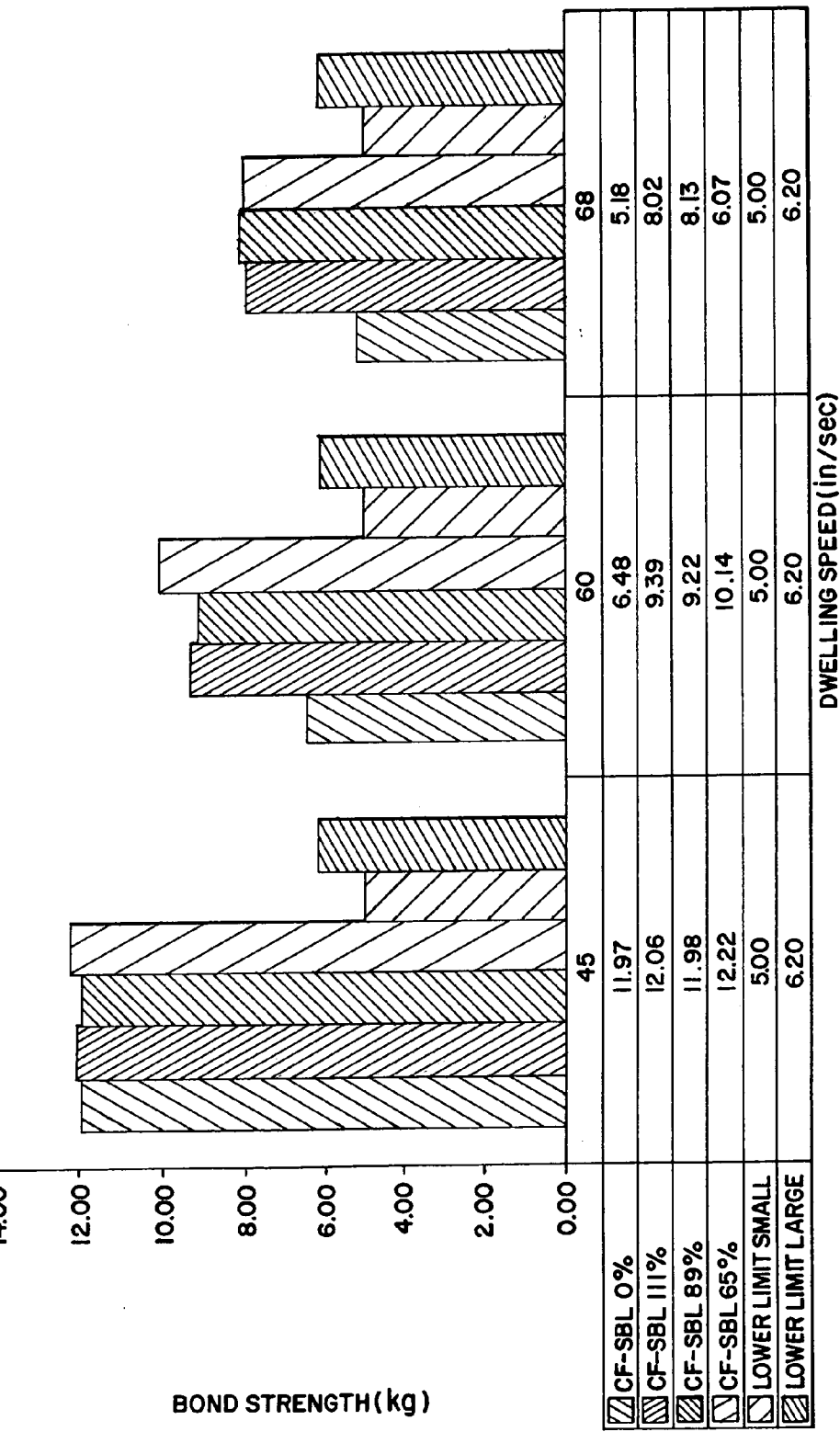

METHOD FOR IMPROVED BOND STRENGTH IN AN ELASTOMERIC MATERIAL

RELATED APPLICATIONS

The present invention relates to a method for improving the strength of ultrasonic bonds in an between two or more layers of elastomeric material. In particular, the invention relates to increasing the strength of ultrasonic bonding in ansuch elastomeric materialmaterials by creating ultrasonic bonds in the materialmaterials while the material is in an elongated statematerials are elongated.

BACKGROUND OF THE INVENTION

Disposable garments, such as infant and children's diapers, swim wear and training pants, as well as adult incontinence garments, conventionally include materials that are joined together and connected using a bonding process. For example, a training pant or other pant-type garment may have a front side panel and a back side panel that are bonded together at a side seam to provide a complete side panel. The side panels are typically connected at the side seam using an ultrasonic process.

The ability to form strong ultrasonic bonds using conventional processes is limited by several factors, including the process converting speeds or production line speeds, bonding time or dwell time, and the thickness and/or basis weight of the materials being bonded.

For particular materials, such as spunbond laminate materials, as the production line speed increases, the dwell time decreases. Consequently, the strength of the ultrasonic bond decreases resulting in insufficient bond strength. Thus, insufficient bond strength may severely limit potential product converting speeds. Additionally, adhesives used to bond spunbond materials and the elastic filaments or fibers used to make such materials elastomeric may inhibit the effectiveness of conventional ultrasonic bonding processes.

Attempts to improve the ultrasonic bonding process have focused on the mechanics of the ultrasonic horn, such as, for example, increasing the energy available from the ultrasonic horn by increasing the horn vibrational amplitude or other design features. However, the mechanical design of the ultrasonic horn may limit the maximum energy that can be delivered by the ultrasonic system to the materials being bonded, thus making it difficult to further enhance the bonding capability of the ultrasonic bonder by modifying the ultrasonic horn and/or the amplifier design. Further attempts to improve ultrasonic bond strength, without sacrificing speed, have included preheating the materials to be bonded prior to the bonding process. However, with heat sensitive materials, such processes cannot be used.

Thus, there is a need for an ultrasonic bonding process that provides sufficient bond strength at increased production line speeds and corresponding decreased dwell times.

SUMMARY OF THE INVENTION

The present invention is directed to a method of increasing the strength of ultrasonic bonds in bonded elastomeric materials at increased production line speeds and bonding dwell times. Specifically, the present invention relates to a method of increasing the ultrasonic bond strength in bonded elastomeric materials by creating the bonds in the material while the material is elongated.

In one embodiment, the method comprises elongating at least a portion of the materials to be bonded, joining the elongated portions of the materials to be bonded together, feeding the materials through an ultrasonic bonding apparatus at a predetermined production line speed, and ultrasonically bonding the elongated portions of the materials while the materials are elongated. Alternatively, the materials may be first joined together, elongated and then ultrasonically bonded.

In particular embodiments, two elastomeric materials are elongated to at least 50% elongation, the materials are brought together and fed through an ultrasonic bonding apparatus at a speed of at least 50 inches/second, and bonded together while the materials in the elongated state to create at least one ultrasonic bond.

Elongating each of the elastomeric materials to be bonded prior to the ultrasonic bonding process results in an increased bond strength between the materials and allows the process to be run at increased speeds. The increased ultrasonic bond strength obtained by the methods of the invention is at least about 7 kg, and preferably, at least about 8 kg.

Further advantages and features of the embodiments of the present invention will be apparent from the following detailed description of the invention in conjunction with the associated drawings. The drawings are merely representative and are not intended to limit the scope or breadth of the appended claims.

BRIEF DESCRIPTION OF THE DRAWINGS

FIG. 2 is a partial plan view of the absorbent garment of FIG. 1 in a partially disassembled, flat state.

FIG. 3 is a partial plan view of the absorbent garment of FIG. 1 in a partially disassembled, flat state.

FIG. 4 schematically illustrates an ultrasonic bonding method according to an embodiment of the invention.

FIGS. 6–9 illustrate test results obtained as set forth in the Examples detailed below.

DETAILED DESCRIPTION OF THE PRESENTLY PREFERRED EMBODIMENTS

The present invention is directed to a method for ultrasonically bonding elastomeric materials. In particular, the present invention is directed to a method for ultrasonically bonding two webs of elastomeric materials, including elastic laminate materials, in which each of the webs to be bonded are elongated prior to ultrasonic bonding.

The method may be used to ultrasonically bond any suitable elastomeric materials together.

For the purposes of this application, elastomeric refers to any material or composite that may be elongated from its relaxed length upon application of force and which will tend to return, at least partially, to its original length, upon release of the applied force.

The method may be used to ultrasonically bond any suitable elastomeric materials together and the principles of the invention may be incorporated into any suitable article requiring bonded layers, such as a disposable pant-type garment. Examples of suitable garments include training pants, diapers, incontinence articles, feminine hygiene articles, disposable clothing, and other personal care articles. In one aspect of the present invention, side seams having increased bond strength of a disposable pant-type garment are formed by ultrasonically bonding front side elastomeric panels to corresponding back side elastomeric panels while at least a portion of each of the panels is elongated. Ultrasonic bond strength adequate for such side seams in a pant-type garment is at least about 5.0 kg. It should be understood that the present method is not limited to the creation of seams in garment type articles, but is applicable to any circumstance in which a strong ultrasonic bond is required between two or more elastomeric materials.

Figure 1:
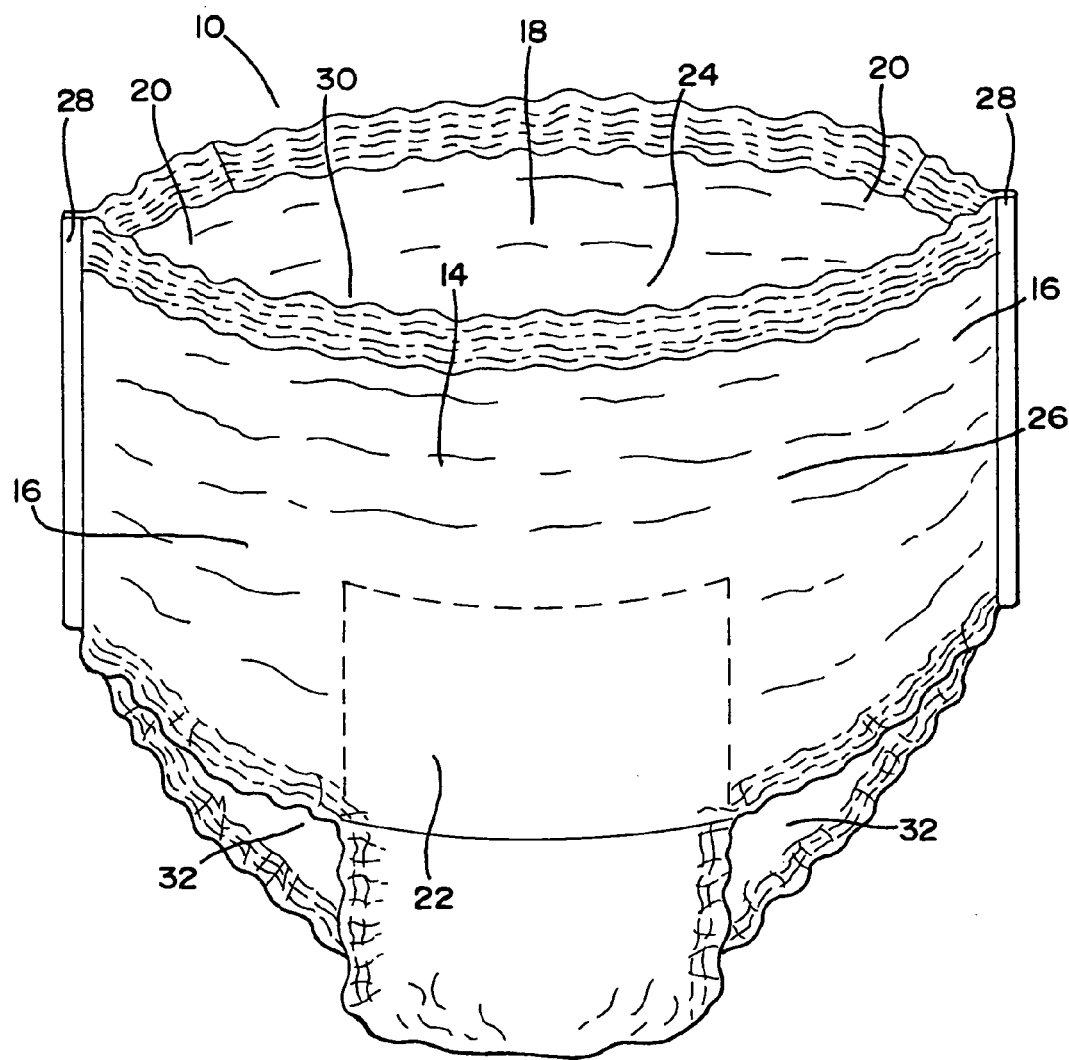
FIG. 1 is a front perspective view of an absorbent garment made according to one aspect of the present invention.

FIG. 1 illustrates a pant-type disposable garment, such as a child's training pant, in a fastened condition. The pant 10 includes an absorbent chassis 12. The chassis 12 includes a front region 14 having two side front panels 16, a back region 18 having two side back panels 20, a crotch region 22 connecting the front region 14 to the back region 18, an inner surface 24 intended to contact the wearer, an outer surface 26 intended to contact the wearer's clothing, and a pair of laterally opposing side seams 28 for securing each front side panel 16 to the corresponding back side panel 20. Preferably, the side seams 28 extend from the waist opening 30 to the leg openings 32 between each front side panel 16 and its corresponding back side panel 20. Alternatively, the side seams 28 may extend along a portion of the side panels 16, 20 from the waist opening 30 to the leg openings 32.

FIGS. 2 and 3 partially illustrate a pant-type 10 garment in a partially disassembled, flat state. Front region 14 and back region 18 are connected to crotch region 22. Front region 14 and back region 18 include those parts of the pant 10, which when worn, are positioned in the front and back of the wearer, respectively. As shown in FIG. 1, the front region 14 and the back region 18 are joined together along seams 28 to define the pant-type garment.

Side panels 16, 20 comprise an elastomeric material that is capable of elongation. Preferably, side panels 16, 20 comprise an elastomeric material that is capable of elongation in a direction that is generally parallel to the transverse axis 34 of the pant 10. Alternatively, side panels 16, 20 may comprise an elastomeric material that is capable of elongation in a direction that is generally parallel to the longitudinal axis 36 of the pant 10. In another embodiment, side panels 16, 20 may comprise an elastomeric material that is capable of elongation in both directions.

Side panels 16, 20 may comprise may comprise any suitable elastomeric material. Preferably, side panels 16, 20 may comprise an elastic spunbond laminate material, for example an elastomeric material including elastic or elastomeric filaments or strands that are disposed between facing layers of spunbond, such as a continuous filament stretch bonded laminate or a vertical filament stretch bonded laminate. Suitable elastomeric materials may include woven or nonwoven elastomeric materials, elastomeric films, elastomeric laminates and combinations thereof. In particular embodiments, the elastic material includes a stretch-thermal laminate (STL), a neck-bonded laminated (NBL), a reversibly necked laminate, or a stretch-bonded laminate (SBL) material. Methods of making such materials are known to those skilled in the art and described in U.S. Pat. No. 4,663,220, U.S. Pat. No. 5,226,992, and European Patent Application No. EP 0 217 032, all of which are incorporated herein by reference. Particularly suitable elastic materials include continuous filament stretch-bonded laminates (CF SBL), as described, for example, in U.S. Pat. No. 5,385,775, and vertical filament stretch-bonded laminates (VF SBL), as described, for example, in PCT International Application WO 01/88245, both of which have been incorporated herein by reference. The side panel material may also include other woven or nonwoven materials, or stretchable but inelastic materials.

Suitable vertical filament stretch-bonded laminates (VF-SBL) comprise a plurality of elastic polymer filaments sandwiched between two facing layers of a spunbond web. Suitable elastic polymer filaments include polymer filaments available from Kraton Polymer, Inc., such as KRATON® G2838 polymer filaments having a basis weight of about 10.5 gsm. The facing layers may each comprise polypropylene spunbond webs having basis weight of about 17 gsm. About 2.0 gsm of Bostik-Findley H2096 adhesive is applied to the facing layers to laminate the filaments to the facing layers and the facing layers to each other.

Suitable continuous filament stretch-bonded laminates (CF-SBL) comprise a meltblown web including a plurality of elastic polymer filaments sandwiched between two facing layers of a spunbond web. Suitable elastic polymer filaments include polymer filaments available from Kraton Polymer, Inc., such as KRATON® 2760 polymer filaments having a basis weight of about 10.5 gsm. The facing layers may each comprise polypropylene spunbond webs having basis weight of about 17 gsm.

In accordance with one aspect of the invention, suitable elastomeric materials are ultrasonically bonded to connect various components of the pant-type garment 10. For example, the side seams 28 may be formed by ultrasonically bonding the front side panels 16 to the back side panels 20, each comprising an elastomeric material such as those described above.

In one embodiment, the front side panels 16 and the back side panels 20 may each comprise an elastic spunbond laminate material such as VF-SBL and CF-SBL. Alternatively, front side panels 16 may comprise an elastomeric material that is different from the material of the back side panels 20.

In accordance with one embodiment of the method, a first web of elastomeric material and a second web of elastomeric material are each elongated. The webs may be elongated from about 25% to about 200%, for example from about 40% to about 150%. Preferably, the webs are elongated from about 50% to about 125%, and more preferably from about 65% to about 111%. In one embodiment, the elastomeric materials are elongated of about 89%. The webs may be elongated independently and then brought together prior to bonding. Alternatively, the webs may be brought together and then elongated.

FIG. 4 schematically illustrates the bonding of two webs of elastomeric materials. As shown, at least two rolls 42, 44 of elastomeric materials 46, 48 are unwound. The materials 46, 48 are brought together in a nip 50 formed between an ultrasonic horn, passed through the ultrasonic bonder 52, over an ultrasonic bonding drum 54, and are ultrasonically bonded. The method of the invention is not limited to the bonding of two layers. Multiple layer composites may also be bonded using the principles of the invention. In addition, a single web of material may be bonded as a multiple layer composite by folding the web one or more times and bonding the folded multiple layers together. Additional layers of unelongated elastomeric materials or nonelastomeric materials may also be included in the multiple layer composite.

Figure 5:
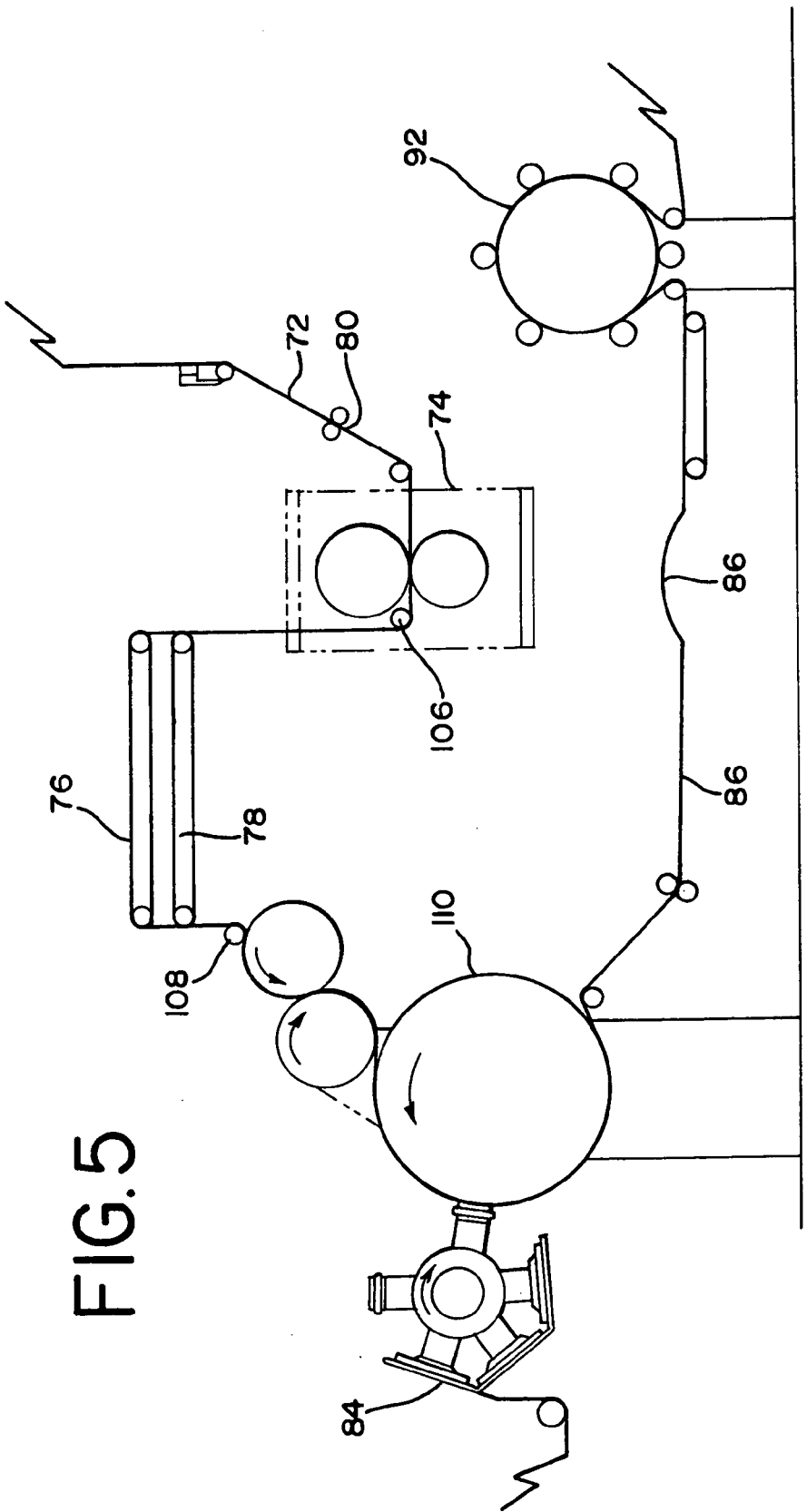
FIG. 5 schematically illustrates, in side elevation, a partial layout of an apparatus for manufacturing the garment of FIG. 1.

Referring to FIGS. 2, 3 and 5, a method for fabricating a pant-type garment having seams ultrasonically bonded in accordance with the present invention is generally illustrated.

Referring to FIG. 5, a web 72 of elastomeric material is cut in a die cutter 74 in a longitudinal direction to form a front and rear body panel web 76, 78. The web of material may be fully or partially elongated to the desired elongation at any point prior to entering the cutter 74, for example the web may be partially or fully elongated at point 80, just prior to entering the cutter 74. In another embodiment, the front and back panel webs 76, 78 may be elongated partially or fully after being cut, but before being bonded. It should be understood that the web or webs of elastomeric materials to be bonded may be elongated at any point after introduction into the fabrication process, so long as the desired elongation is made at some point prior to bonding.

In one embodiment, the front and rear body panel webs 76, 78 are separated such that no portions of either web overlap each other so as to create a gap 82 between the webs 76, 78, as shown in FIGS. 2 and 3. For example, and referring to FIG. 5, in one embodiment, a first pair of rollers 106 can be angled or twisted to laterally spread the front and rear body panel webs 76, 78 a first amount before they are shifted in the longitudinal machine direction. A second pair of rollers 108 can be angled or twisted to laterally spread the front and rear body panel webs 76, 78 a second amount after they are shifted in the longitudinal machine direction. Of course, it should be understood that the front and rear body panels can be first shifted in the longitudinal machine direction the desired amount and then separated in the lateral cross direction the entire desired amount, or they can also be first separated in the lateral cross direction the entire desired amount and then shifted in the longitudinal machine direction.

After the body panel webs 76, 78 are aligned and separated, regardless of the order thereof, a plurality of crotch members 84, for example absorbent inserts, are positioned in the lateral cross direction so as to bridge the gap 82 between the body panel webs 76, 78. It should be understood that the term "gap" as used herein includes a "zero" distance between the respective cut edges, wherein the cut edges abut but do not overlap. The crotch members 84 are secured to the body panel webs 76, 78. For example, the absorbent inserts, may be assembled offline and are then applied to the front and rear body panel webs 76, 78 as those webs are carried by a construction drum 110.

Referring to FIGS. 2, 3 and 5, after the crotch members 84 are secured to the body panel webs 76, 78, the assembly is conveyed on a conveyor 86 and are successively folded 86 such that the front and rear body panel webs 76, 78 are positioned in an overlapping, or overlying relationship, preferably with the outer edges 88 and 90 aligned. The folded webs 76, 78 are then ultrasonically bonded in a suitable ultrasonic bonding unit 92. The webs are then cut and prepared for packaging (not shown).

Methods and apparatus for fabricating a disposable garment are further disclosed in U.S. Pat. Nos. 5,761,478, 5,759,340, and 6,139,004, U.S. patent application Ser. No. 10/038,766, entitled "Apparatus For Applying Discrete Parts to A Moving Web," filed Jan. 2, 2002, and U.S. Pat. No. 6,979,380, entitled "Three-Piece Disposable Undergarment and Method for the Manufacture Thereof, filed Oct. 1, 2002, all of which are assigned to Kimberly-Clark Worldwide, Inc., the assignee of the present application, and the entire disclosures of all of which are hereby incorporated herein by reference.

The ultrasonic bonding unit may comprise any suitable ultrasonic bonding apparatus, including a plunge-type ultrasonic bonder or a rotary-type ultrasonic bonder. Suitable rotary ultrasonic bonding apparatus include those apparatus disclosed in U.S. Pat. Nos. 5,096,608; 5,110,403; 5,660,679; and 5,667,608, the disclosures of which are incorporated herein by reference. For example, as shown schematically in FIG. 4, the ultrasonic bonding apparatus 52 may comprise a drum 54, mounted for rotation about a first axis in a given direction and having a circumferential outer working surface 56. An ultrasonic anvil (not shown) may be mounted on the drum 54 at the outer working surface 56 and an ultrasonic horn 58 is mounted for rotation with the drum 54 in a direction that is transverse with the direction of the rotation of the drum to extend over and operate in combination with the anvil to apply ultrasonic energy to the workpiece 60. Within the ultrasonic bonding apparatus 52, the elongated webs are ultrasonically bonded together and a material 62, connected by at least one ultrasonic bond, exits the ultrasonic bonding apparatus. As a result of passing the webs through the ultrasonic bonding apparatus in an elongated state, a predetermined bond strength can be formed.

The webs are passed through the ultrasonic bonding apparatus at a speed of about 10 to about 100 inches/second and at a bonding or dwell time of from about 0.20 to about 3.0 seconds. The bonding or dwell time is the amount of time that the webs are positioned between the ultrasonic horn and the anvil. Preferably, the webs are passed through the ultrasonic bond apparatus at a speed of at least about 50 inches/second and, more preferably, at a speed of at least about 60 inches/per second, depending on the ultrasonic bonding apparatus used. In one embodiment, the speed is at least about 68 inches/second. The dwell time is preferably from from about 0.26 to about 2.6 seconds.

In the following examples, elongated elastomeric webs were ultrasonically bonded at various elongations and production line speeds. The examples are exemplary and presented for purposes of illustration only. These examples are not intended in any limiting sense.

EXAMPLES

Example 1

VF-SBL materials comprising KRATON® G2838 polymer filaments having a basis weight of about 10.5 gsm sandwiched between two facing layers, each comprising polypropylene spunbond webs having basis weight of about 17 gsm, and 2.0 gsm of Bostik-Findley H2096 adhesive, were ultrasonically bonded. The final or total basis weight of the samples was about 48 gsm in the restracted or gathered state.

The specimens, which comprised two layers of the VF-SBL materials, were elongated to elongations of 111% (14" to 29.5"); 89% (16" to 26.5"), and 65% (16" to 26.5) and were bonded using a using a 1" stationary rotary bonder having the following specifications:

| Frequency | 40 kHz |
|---|---|
| Power | 500 watt |
| Air pressure | 24 psi |
| Horn length | 3.6" |
| Horn Diameter | 3.5" |
| Horn Width | 1.0" |

-continued

| Horn peak to peak amplitude | 0.005–0.002" (waiting for confirmation) |
|---|---|

The samples were produced at speeds of 45, 60 and 68 inches per second. The results in Table 1 (and shown graphically at FIGS. 6 and 7) display the average bond strength in kilograms for the bonded VF SBL. Six inch samples of the bonded laminate were placed between two opposing jaws of a Chatillon® tensile tester available from Amtek Inc. The jaws of the Chatillon tensile tester operate to pull the bonded layers apart. The amount force require to break the ultrasonic bond was then recorded in kilograms as set forth below.

TABLE 1

Average Ultrasonic Bond Strength (kg)

| Speed | 0% Elongation | 65% Elongation | 89% Elongation | 111% Elongation |
|---|---|---|---|---|
| 45 in./sec. | 7.9 kg. | 13.04 kg. | 13.17 kg. | 11.07 kg. |
| 60 in./sec. | 1.9 kg | 8.2 kg | 9.49 kg | 8.45 kg |
| 68 in./sec. | 1.53 kg | — | 7.55 kg | 8.21 kg |

As shown in Table 1 and FIGS. 6 and 7, elongating the VF-SBL specimens prior to ultrasonic bonding resulted in improved ultrasonic bond strength at increased speeds. As shown in Table 1 and FIGS. 6 and 7, the bond strength significantly exceeds that required to provide adequate strength in pant-type garments including the VF-SBL material.

Example 2

CF-SBL materials comprising KRATON® G2760 polymer filaments having a basis weight of about 10.5 gsm, sandwiched between two facing layers, each comprising polypropylene spunbond webs having basis weight of about 17 gsm, were ultrasonically bonded. The final or total basis weight of the samples was about 37 gsm in the restracted or gathered state.

The specimens, which comprised two layers of the CF-SBL materials, were elongated to elongations of 111% (14" to 29.5"); 89% (16" to 26.5"), and 65% (16" to 26.5) and were bonded using a using the 1" stationary rotary bonder described in Example 1.

The samples were produced at speeds of 45, 60 and 68 inches per second. The results in Table 2 (and shown graphically at FIGS. 8 and 9) display the average bond strength in kilograms for the bonded CF-SBL materials. The bond strengths were measured in accordance with the test method set forth in Example 1.

TABLE 2

Average Ultrasonic Bond Strength (kg)

| Speed | 0% Elongation | 65% Elongation | 89% Elongation | 111% Elongation |
|---|---|---|---|---|
| 45 in./sec. | 11.97 kg. | 12.06 kg. | 11.96 kg. | 12.22 kg. |
| 60 in./sec. | 6.48 kg | 9.39 kg | 9.22 kg | 10.14 kg |
| 68 in./sec. | 5.18 kg | 8.02 kg | 8.13 kg | 8.07 kg |

As shown in Table 2 and FIGS. 8 and 9, elongating the CF-SBL specimens prior to ultrasonic bonding resulted in improved ultrasonic bond strength at increased speeds. As shown in Table 2 and FIGS. 8 and 9, the bond strength significantly exceeds that required to provide adequate strength in pant-type garments including the CF-SBL material.

It is therefore intended that the foregoing detailed description be regarded as illustrative rather than limiting, and that it be understood that it is the following claims, including all equivalents, that are intended to define the spirit and scope of the invention.

The invention claimed is:

1. A method of increasing the strength of ultrasonic bonds in a web of elastomeric material, the method comprising:
   elongating a first elastomeric material to a first elongation from about 25% to about 200%;
   elongating a second elastomeric material to a second elongation from about 25% to about 200%;
   feeding the first elastomeric material and the second elastomeric material through an ultrasonic bonding apparatus at a predetermined speed and dwell time; and
   ultrasonically bonding the first elastomeric material to the second elastomeric material while the materials are elongated to form at least one ultrasonic bond having a bond strength of at least about 6 kg.

2. The method of claim 1 where the first elastomeric material and the at least second elastomeric material are elongated to the same degree.

3. The method of claim 1 where the first elastomeric material and the at least second elastomeric material are elongated to an elongation from about 40% to about 150%.

4. The method of claim 3 where the first elastomeric material and the at least second elastomeric material are elongated to an elongation from about 50% to about 125%.

5. The method of claim 4 where the first elastomeric material and the at least second elastomeric material are elongated to an elongation from about 65% to about 111%.

6. The method of claim 5 where the first elastomeric material and the at least second elastomeric material are elongated to an elongation of about 89%.

7. The method of claim 1 where the speed is at least about 50 inches/second.

8. The method of claim 7 where the speed is at least about 55 inches/second.

9. The method of claim 8 where the speed is at least about 60 inches/second.

10. The method of claim 9 wherein the speed is about 68 inches/second.

11. The method of claim 1 where the ultrasonic bond has a bond strength of at least about 7 kg.

12. The method of claim 11 where the ultrasonic bond has a bond strength of at least about 8.0 kg.

13. The method of claim 1 where at least one of the first and the second materials comprises a stretch bonded laminate.

14. The method of claim 13 where at least one of the first and the second materials comprises a vertical filament stretch bonded laminate.

15. The method of claim 13 where at least one of the first and the second materials comprises a continuous filament stretch bonded laminate.

16. The method of claim 1 where at least one of the first and the second material comprises an elastomeric film.

17. The method of claim 16 where the elastomeric film is selected from the group consisting of polyesters, polyolefins, and combinations thereof.

18. The method of claim 1 where the elongated first material is ultrasonically bonded to the elongated second material using a plunge ultrasonic bonder.

19. The method of claim 1 where the elongated first material is ultrasonically bonded to the elongated second material using a rotary ultrasonic bonder.

20. The method of claim 1 where at least one of the elastomeric materials is elongated longitudinally.

21. The method of claim 1 where at least one of the elastomeric materials is elongated transversely.

22. The method of claim 1 where at least one of the elastomeric materials is elongated both longitudinally and transversely.

23. The method of claim 1 where the two webs of elastomeric materials comprise a single sheet of material that has been folded at least once to create two or more layers.

24. The method of claim 1 where the dwell time is from about 0.20 seconds to about 3.0 seconds.

25. The method of claim 24 where the dwell time is from about 0.26 seconds to about 2.6 seconds.

26. A method of increasing the strength of ultrasonic bonds in a web of elastomeric material, the method comprising:
   elongating a first elastomeric material to a first elongation;
   elongating at least a second elastomeric material to a second elongation;
   feeding the elastomeric materials through an ultrasonic bonding apparatus at a production line speed of at least about 55 inches/second; and
   ultrasonically bonding a portion of the first elastomeric material to a portion of the at elastic second elastomeric material while the materials are elongated to form an ultrasonic bond having a bond strength of at least about 6 kg.

27. A method of increasing the strength of ultrasonic bonds in a web of elastomeric material, the method comprising:
   elongating a first elastomeric material from about 25% to about 200%;
   elongating at least a second elastomeric material from about 25% to about 200%;
   feeding the elastomeric materials through an ultrasonic bonding apparatus at a predetermined speed and bond dwell time; and
   ultrasonically bonding the first elastomeric material to the at least second elastomeric material while the materials are elongated to form at least one ultrasonic bond having a bond strength of at least about 6 kg.

28. An apparatus for ultrasonically bonding at least two webs of elastomeric material comprising:
   a first elongating unit operative to elongate at least a portion of a first web of elastomeric material to an elongation of from about from about 25% to about 200%;
   at least a second elongating unit operative to elongate at least a portion of a second web of elastomeric material to an elongation of from about from about 25% to about 200%;
   an ultrasonic bonding unit operative to ultrasonically bond the elongated portion of the first web to the elongated portion of the second web to a bond strength of at least about 6 kg.

29. A method of increasing the ultrasonic bond strength in the side seams of a pant-type garment comprising:
   providing a web of elastomeric material;
   elongating the web of elastomeric material to a predetermined elongation of from about from about 25% to about 200%;
   cutting the web of elastomeric material to form an elongated front elastomeric panel having a first longitudinal side edge and a second longitudinal side edge and an elongated back elastomeric panel having a first longitudinal side edge and a second longitudinal side edge;
   attaching an absorbent structure to the elongated front and back elastomeric panels to form an absorbent composite having a longitudinal axis and a transverse axis;
   folding the absorbent composite along the transverse axis of the composite; and
   ultrasonically bonding the first side edge of the front panel to the first side edge of the back panel and the second side edge of the front panel to the second side edge of the back panel while the panels are elongated to form side seams;
   wherein the side seams comprise at least one ultrasonic bond having a bond strength of at least about 6 kg.

* * * * *